US007550282B2

(12) United States Patent
Margel et al.

(10) Patent No.: US 7,550,282 B2
(45) Date of Patent: Jun. 23, 2009

(54) BIOLOGICAL GLUE BASED ON THROMBIN-CONJUGATED NANOPARTICLES

(75) Inventors: Shlomo Margel, Rehovot (IL); Larisa Sheihet, Tel-Aviv (IL); Tamar Tennenbaum, Rosh Ha'ain (IL)

(73) Assignee: Bar-Ilan University, Ramat Gan (IL)

( * ) Notice: Subject to any disclaimer, the term of this patent is extended or adjusted under 35 U.S.C. 154(b) by 135 days.

(21) Appl. No.: 10/534,469

(22) PCT Filed: Nov. 18, 2003

(86) PCT No.: PCT/IL03/00977

§ 371 (c)(1),
(2), (4) Date: Nov. 16, 2005

(87) PCT Pub. No.: WO2004/045494

PCT Pub. Date: Jun. 3, 2004

(65) Prior Publication Data

US 2006/0104970 A1 May 18, 2006

Related U.S. Application Data

(60) Provisional application No. 60/427,545, filed on Nov. 20, 2002.

(51) Int. Cl.
*C12N 9/50* (2006.01)
*A61K 38/46* (2006.01)
(52) U.S. Cl. ..................... 435/219; 424/94.67
(58) Field of Classification Search .......... 435/219; 424/94.64
See application file for complete search history.

(56) References Cited

U.S. PATENT DOCUMENTS

| 5,916,596 | A | 6/1999 | Desai et al. |
| 6,552,172 | B2* | 4/2003 | Marx et al. ............ 530/382 |
| 7,220,401 | B2* | 5/2007 | Lanza et al. ........... 424/9.323 |
| 2002/0119572 | A1* | 8/2002 | Jacobson et al. ....... 435/466 |
| 2003/0045690 | A1 | 3/2003 | Marx et al. |
| 2003/0138490 | A1 | 7/2003 | Hu et al. |
| 2003/0219786 | A1* | 11/2003 | Hallahan et al. ........ 435/6 |

FOREIGN PATENT DOCUMENTS

| WO | 99/62079 A1 | 12/1999 |
| WO | 03/037248 A2 | 5/2003 |

OTHER PUBLICATIONS

International Search Report for PCT/IL03/00977 dated Aug. 9, 2004.
Brandriss et al. "Synthesis and Characterization of Self-Assembled Hydrophoic Monolayer Coatings on Silica Colloids", American Chemical Society, 1993, reprinted from Langmuir, 1993, vol. 9, No. 5, pp. 1232-1240.
Melamed et al. "Poly(N-vinyl α-phenylalanine) Microspheres: Synthesis, Characterization, and Use for Immobilization and Microencapsulation", Journal of Colloid and Interface Science, 241, pp. 357-365, 2001.
Horák et al. "Biologically Active Thrombin-Containing Hydrogels Based on Poly(2-hydroxyethyl methacrylate) for Endovascular Occlusion", Polymers in Medicine, 1991, vol. XXI, No. 1-2, pp. 31-40.
Bamnolker et al. "Dispersion Polymerization of Styrene in Polar Solvents: Effect of Reaction Parameters on Micropshere Surface Composition and Surface Properties, Size and Size Distribution, and Molecular Weight", Journal of Polymer Science: Part A: Polymer Chemistry, vol. 34, 1857-1871, 1996, John Wiley & Sons.
Parrado et al., "Immobilization-Stabilization of Kerase, a Serine Protease from *Streptomyces fradiae*, by Covalent Attachment to Porous Glass", Biosic. Biotech. Biochem., 59 (5), pp. 906-907, 1995.
Müller et al. "Intravenously Injected Particles: Surface Properties and Interaction with Blood Proteins—The Key Determining the Organ Distribution", Scientific and Clinical Applications of Magnetic Carriers, Plenum Press, New York, 1997, pp. 135-148.
Bendikiene et al. "Stabilization of Serine Proteases by Immobilization", Stability and Stabilization of Biocatalysts, 1998, Elsevier Science B.V., pp. 583-588.
Grüttner et al., "Preparation and Characterization of Magnetic Nanospheres for In Vivo Application", Scientific and Clinical Applications of Magnetic Carriers, Plenum Press, New York, 1997, pp. 53-67.
Margel et al., "Synthesis, Characterization, and Use of New Solid and Hollow, Magnetic and Non-Magnetic, Organic-Inorganic Monodispersed Hybrid Microspheres", Scientific and Clinical Applications of Magnetic Carriers, Plenum Press, New York, 1997, pp. 37-51.
Margel et al., "Functional Nanospheres: Synthesis and Biological Applications", Recent Res. Devel. In Polymer Science, 1 (1997), pp. 51-78.
Sugitachi et al., "New Materials for Hemostasis", Progress in Artificial Organs—1985, ISAO Press, Cleveland 1986, pp. 1020-1023.
Liu et al., "Gold Labeling of Thrombin and Ultrastructural Studies of Thrombin-Gold Conjugate Binding by Fibrin", Analytical Biochemistry 147, 1985, pp. 49-56.
Stöber et al., "Controlled Growth of Monodisperse Silica Spheres in the Micron Size Range", Journal of Colloid and Interface Science 26, 1968, pp. 62-69.
Per Wikstrom et al, "Gas Phase Silylation; A Rapid Method For Preparation of High-Performance Liquid Chromatography Supports", Elsevier Science Publishers B.V., Journal of Chromatography, 455 (1988) 105-117.
Oliver Lowry et al, "Protein Measurement With the Folin Phenol Reagent", J. Biol. Chem. 193, p. 265-275 (1951).

* cited by examiner

*Primary Examiner*—Ruth A Davis
(74) *Attorney, Agent, or Firm*—Nixon & Vanderhye P.C.

(57) ABSTRACT

Thrombin-conjugated nanoparticles, wherein said nanoparticles comprise one or more organic and/or inorganic compounds and process for preparing the same are provided. The thrombin-conjugated nanoparticles are suitable for use in the preparation of fibrin-based biological sealant.

14 Claims, 7 Drawing Sheets

BIOLOGICAL GLUE BASED ON THROMBIN-CONJUGATED NANOPARTICLES

This application is the U.S. national phase of international application PCT/IL2003/000977 filed 18 Nov. 2003 which designated the U.S. and claims benefit of U.S. Provisional Application 60/427,545, filed 20 Nov. 2002, the entire contents of each of which are hereby incorporated by reference.

FIELD OF THE INVENTION

The present invention relates to thrombin-conjugated nanoparticles and formulations comprising the same, which are suitable for the preparation of fibrin-based biological glue.

BACKGROUND OF THE INVENTION

The art has recognized the potential of nanoparticles, which are generally defined as spherical particles having sizes ranging from approximately a few nanometers up to a few microns, for use in different applications in chemistry, biology and medicine. The preparation of various nanoparticles and uses thereof are described in the following publications: Scientific and Clinical Applications of Magnetic Carriers, Ed. U. Hafeli, W. Schutt, J. Teller and M. Zborowski, Plenum Press, N.Y. 37-51, 53-67 and 135-148 (1997); Recent Res. Developments in Polymerization Science, Ed. S. G. Patidalai, Transworld Research Network 1, 51-78 (1997); O. Melamed and S. Margel, J. of Colloid and Interface Science 241, 357 (2001); V. Bendikiene and B. Juodka, Stability and Stabilization of Biocatalysts, Ed. A. Ballesteros, F. J. Plou, J. L. Iborra and P. J. Halling, Elsevier Science 583-588 (1998) and J. Parrado and J. Bautista, Biosci Biotech. Biochem. 59 (5), 906 (1995).

The blood clotting process involves the cleavage of the plasma highly soluble molecule fibrinogen by the action of the proteolytic enzyme thrombin, following which the monomers obtained associate together to form fibrin, in the form of long, insoluble fibers. The formation of the insoluble fibrin matrix may be accelerated by the presence of factor XIII and/or the presence of $Ca^{+2}$ ions. Thrombin converts factor XIII to factor XIIIa, which, in the presence of $CaCl_2$, crosslinks the fibrin matrix to give a highly crosslinked polymer.

The art proposed various formulations, known as fibrin glues, or fibrin sealants, in order to allow effective and rapid interaction between fibrinogen and thrombin, and devices useful for delivering said formulations to the bleeding site, thereby mimicking the final step of blood clotting process resulting in the production of the desired fibrin clot.

For example, the commercially available product Tisseel® Fibrin Sealant (Immuno AG, Austria) is based on a two compartments syringe for separately holding a thrombin solution and fibrinogen solution. In use, the two components are simultaneously mixed and applied on the bleeding area to form the insoluble fibrin glue matrix.

Another commercially available product, Quixil® (Omrix Biopharmaceuticals, Belgium) is based on one-compartment syringe, or similar arrangement, composed of a thrombin solution only. The thrombin solution may also contain other components, e.g. antifibrinolytic agents such as aprotinin or tranexamic acid and/or factor XIII and/or $CaCl_2$. The thrombin solution is then sprayed, or compressed, or applied, on the bleeding area to form the insoluble fibrin by interacting with the fibrinogen content of the blood.

TachoComb® (NYCOMED GmbH, Munchen), is prepared by covering a sheet of collagen with human fibrinogen and bovine thrombin. Aprotinin is added to prevent early degradation of the fibrin clot by plasmin. For this purpose, the solid components: fibrinogen, thrombin and aprotinin are dispersed in an organic medium, and the suspension is applied on a sheet of collagen. The organic medium is evaporated, leaving a dried layer of the components of fibrin glue adsorbed on the collagen surface. When the coating comes in contact with blood or other liquids, the components dissolve and fibrin is formed.

A. Sugitachi et al. [Progress in Artificial Organs, Ed. Y. Nose, C. Kjellstrand and P. Ivanovich, 1020-1022 (1985)] describe dry fine flakes containing thrombin, gelatin and factor XIII, suitable for treating hemostasis.

Horak et al. [Polymers in Medicine 21 (1-2), 31 (1991)] describe a thrombin-containing hydrogel, based on poly(2-hydroxyethyl methacrylate), that is useful for endovascular occlusion.

Liu et al. [Analytical Biochemistry 147, 49 (1985)], describe thrombin-gold nanoparticles, that are prepared by physical adsorption of a monolayer of thrombin onto gold nanoparticles of 16.5±1.8 nm diameter.

It is a purpose of the present invention to provide a novel thrombin formulation and therapeutic compositions based thereon, that may be used in the preparation of a fibrin sealant.

It is another purpose of the invention to provide a thrombin formulation that is highly stable and easily deliverable, and a process for preparing the same.

It is a further purpose of the invention to provide a thrombin formulation that permits rapid formation of the fibrin clot.

Further objects and advantages of the present invention will become apparent as the description proceeds.

SUMMARY OF THE INVENTION

The present invention is primarily directed to thrombin-conjugated nanoparticles, wherein said nanoparticles comprise one or more organic and/or inorganic compounds.

The term "thrombin-conjugated nanoparticles", as used herein, refers to nanoparticles to which thrombin molecules are linked, either chemically (e.g., covalently), or by means of physical adsorption.

The nanoparticles comprise organic compounds, wherein said organic compounds are preferably selected from the group consisting of proteins and synthetic polymers, and/or inorganic compounds, wherein said inorganic compounds are preferably selected from the group consisting of metal oxides or oxides of metalloids.

Preferably, the nanoparticles are selected from the group consisting of iron oxide-containing nanoparticles, albumin nanoparticles, solid or hollow silicon oxide nanoparticles and nanoparticles made of organic polymeric core coated with at least one silica shell, optionally having a magnetic layer interposed between said core and said silica shell. Preferably, the average diameter of the thrombin-conjugated nanoparticles is not greater than 5 µm.

According to one preferred embodiment, the invention provides thrombin-conjugated nanoparticles, wherein the thrombin molecules are covalently-bonded to the surface of the nanoparticles.

According to another preferred embodiment, the invention provides thrombin-conjugated nanoparticles, wherein the thrombin molecules are covalently-bonded to spacer arms, and wherein said spacer arms are covalently-linked to the surface of the nanoparticles. Most preferably, the spacer arm is albumin.

According to another preferred embodiment, the invention provides thrombin-conjugated nanoparticles, wherein the thrombin molecules are physically adsorbed onto spacer arms, and wherein said spacer arms are covalently-linked to the surface of the nanoparticles. Most preferably, the spacer arm is albumin.

Optionally, the thrombin-conjugated nanoparticles according to the invention may further comprise a pharmaceutical agent which is either encapsulated within said nanoparticles or bound thereto.

In another aspect, the present invention relates to a process for preparing thrombin-conjugated nanoparticles, comprising providing nanoparticles having reactive chemical groups on their surface, and either covalently linking thrombin thereto, or covalently linking spacer arms to said reactive chemical groups and subsequently allowing thrombin molecules to chemically react with said spacer arms, or to become physically adsorbed thereto. Preferably, the reactive chemical groups are either activated carbon-carbon double bonds or aldehyde groups. Preferably, the spacer arm is albumin.

In another aspect, the present invention provides a therapeutic composition comprising thrombin-conjugated nanoparticles, suitable for use in the preparation of fibrin-based biological sealant. According to one variant, the therapeutic composition is provided in the form of a dry powder comprising nanoparticles, to which thrombin is conjugated, and a dispersant, which is most preferably gelatin. It has been surprisingly found that such a formulation exhibits excellent storage stability and may be effectively used in the preparation of fibrin-based biological sealant. In another variant, the therapeutic composition is provided in the form of a liquid suspension comprising the thrombin-conjugated nanoparticles.

In another aspect, the present invention provides a process for preparing a thrombin formulation provided in the form of a dry powder comprising thrombin-conjugated nanoparticles, wherein said process comprises providing an aqueous suspension of said thrombin-conjugated nanoparticles and drying the same in the presence of a suitable dispersant, which is preferably gelatin. Preferably, the drying is accomplished by means of lyophilization.

In another aspect, the present invention provides a method for preparing a fibrin-containing biological sealant, wherein said method comprises contacting thrombin-conjugated nanoparticles, which preferably have an average diameter smaller than 5µ, with fibrinogen. Preferably, the thrombin conjugated nanoparticles and fibrinogen are contacted in a liquid medium selected from the group consisting of aqueous solution, plasma or blood, whereby the fibrin sealant is formed. According to a preferred embodiment of the invention, the thrombin-conjugated nanoparticles and fibrinogen are contacted in the presence of calcium ions or factor XIII.

The fibrin biological sealant formed according to the present invention is typically characterized by the presence of nanoparticles, the average diameter of which being preferably smaller than 5 µm, within its polymeric matrix.

DETAILED DESCRIPTION OF PREFERRED EMBODIMENTS

Figure 1A:
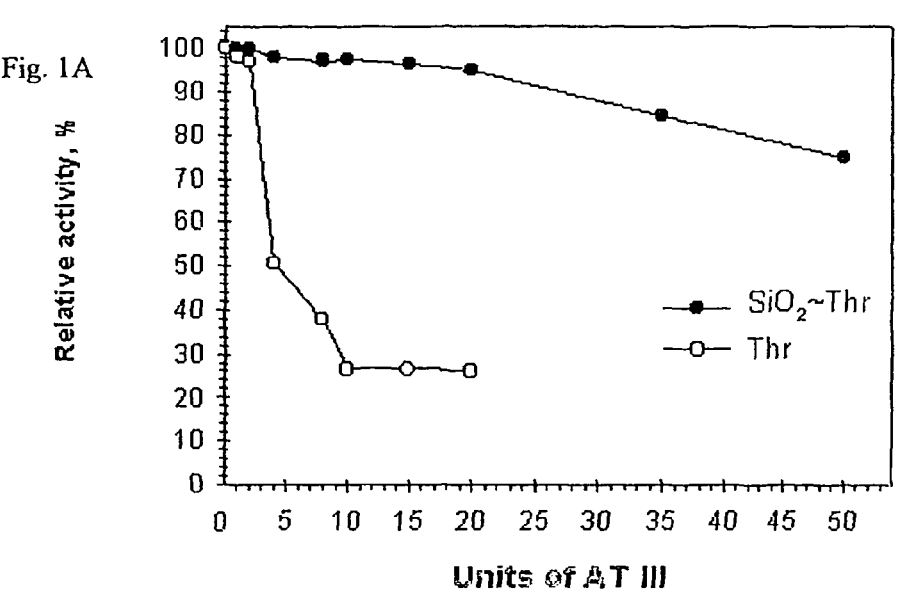
FIG. 1. Effect of the inhibitor Antithrombin III on the activity of Thr and immobilized Thr: $SiO_2$~Thr (2.3 µm) (A), AB~Thr (B) and Mag~Thr (C) suspended in PBS.

The present invention involves the synthesis of various nanoparticles, the introduction of reactive chemical groups onto the surface of said nanoparticles, wherein said reactive chemical groups are most preferably aldehyde groups and carbon-carbon activated double bonds, and the subsequent attachment of thrombin molecules onto said modified surface, either covalently or physically, as will be described in more detail below.

According to one preferred embodiment of the invention, the nanoparticles comprise iron oxide. Magnetic iron oxide-containing nanoparticles (hereinafter sometimes desiganted Mag nanoparticles or Mag) may be prepared following the synthetic procedures described by Margel et al. in international publication no. WO 99/62079, incorporated herein by reference, according to which a suitable polymeric chelating agent, such as gelatin, is contacted in aqueous solution with a source of iron ions under well-defined conditions, to yield Mag nanoparticles having diameters ranging from 15 to 100 nm. The introduction of reactive chemical groups onto the surface of the Mag nanoparticles may be accomplished by the methods described in WO 99/62079, according to which said nanoparticles are treated with dextran or gelatine to form a functional coating thereon, which contains suitable reactive groups that may be used for the subsequent attachment of thrombin. Alternatively, following the formation of the dextran coating, a suspension of the coated Mag nanoparticles is reacted with suitable reagents, capable of forming new chemically reactive groups on said dextran coating. Particularly preferred reagents are oxidizing agents or divinyl sulfone (DVS) or derivatives thereof. Preferably, the dextran-coated Mag nanoparticles are reacted with divinyl sulfone at elevated temperature, under alkaline pH, whereby reactive carbon-carbon double bonds are obtained on said nanoparticles.

According to another preferred embodiment of the invention, the nanoparticles are made of albumin (hereinafter sometimes designated AB nanoparticles or AB). Albumin nanoparticles may be prepared by adding an appropriate organic solvent into an aqueous solution of human serum albumin at room temperature, whereby the albumin is caused to precipitate. Thereafter, the temperature is preferably raised, in order to harden the albumin particles. The size of the AB nanoparticles may be controlled by changing experimental parameters such as albumin concentration or organic solvent type. Typical concentration of the albumin in the aqueous solution is in the range of 2%-4% (w/w). Preferred organic solvents that may be used for the precipitation of albumin are lower alkanols, such as ethanol. The introduction of reactive chemical groups onto the surface of the AB nanoparticles is most preferably accomplished by reacting said AB nanoparticles with glutaraldehyde (GA) or DVS and derivatives thereof, to obtain aldehyde reactive groups or carbon-carbon double bonds on said surface, respectively.

According to another preferred embodiment of the invention, the nanoparticles comprise silica. Hereinafter, these silica containing nanoparticles are sometimes designated $SiO_2$ nanoparticles or $SiO_2$.

In one preferred variant, the $SiO_2$ nanoparticles are provided in the form of an organic polymeric core coated with one or more silica shells, optionally having a magnetic layer interposed between said core and said silica shell(s). Preferably, the organic core comprises a polymer selected from the group consisting of polystyrene, polymethylmetacrylate, polychloromethylstyerne and polyvinyltoluene. Suitable synthetic routes for the preparation of said nanoparticles are described by H. Bamnolker and S. Margel [J. of Polymer Science, Polymer Chemistry 34, 1857 (1996) and U.S. Pat. No. 6,103,379] and S. Brandriss and S. Margel [Langmuir 9, 1232 (1993)], which are incorporated herein by reference. A preferred procedure involves the dispersion polymerization of a suitable monomer, such as styrene, in ethanol in the presence of polyvinylpyrrolidone as surfactant, to give monodispersed polystyrene microspheres of diameter ranging between 0.3-6 μm, following which silica nanoparticles of substantially smaller size (ca. 30 nm) are coated on the polystyrene particles by seeded polymerization of tetraethoxysilane on the surface of said polystyrene particles, using the Stober method. If desired, an intermediate magnetic layer may be interposed between the organic core and the silica coating by means of seeded polymerization of iron salts on said core according to a procedure similar to that described by Margel et al. [Scientific and Clinical Applications of Magnetic Carriers, Ed. U. Hafeli, W. Schutt, J. Teller and M. Zborowski, Plenum Press, N.Y. 37-51 (1997)]. Optionally, hollow silica nanoparticles may be obtained by burning the organic core according to the methods described in U.S. Pat. No. 6,103,379.

In a second preferred variant, silica nanoparticles having diameters in the range of 10-100 nm are provided. These nanoparticles are conveniently prepared by polymerization of $Si(OEt)_4$ according to the Stober Method (see, for example, Stober et al., J. of. Colloid and Interface Science, 26, p. 62 (1968) and Brandriss and Margel, Langmuir 9, 1232 (1993), which are incorporated herein by reference). $SiO_2$ nanoparticles of different sizes within the range of 10-100 nm are prepared by changing the Stober polymerization conditions, i.e. the monomer [$(Si(OEt)_4$] concentration, the water concentration, ammonia, etc, as described in detail in the aforementioned publications The introduction of reactive chemical groups onto the surface of the silica nanoparticles (either the silica nanoparticles that are provided in the form of organic polymeric core coated with one or more silica shells, optionally having magnetic layer interposed between said core and said silica shell(s), or the silica nanoparticles having diameters in the range of 10-100 nm) may be carried out according to the procedures described by Brandriss and Margel [Langmuir 9, 1232 (1993)]. According to one preferred procedure, the silica nanoparticles are mixed together with a reagent of the formula $Si(O-Alk)_3(CH_2)nNH_2$, wherein Alk is a lower alkyl group, which is most preferably methyl or ethyl, and n is an integer varying from 2 to 10, in a suitable organic solvent, which is most preferably a lower ($C_1$-$C_4$) alkanol, at a temperature in the range of 20 to 50° C. for several hours, following which the nanoparticles are washed to remove excess of reagents therefrom. Alternatively, the reaction between the silica-containing nanoparticles and the reagent of the formula $Si(O-Alk)_3(CH_2)nNH_2$ as defined above is carried out in aqueous solution under suitable conditions, and most preferably in acetate buffer at pH 5.5, according to the description of Wiksteron et al. [J. of Chromatography 455, p. 105 (1988)]. The resulting silica nanoparticles have primary amino groups on their surface, which are subsequently reacted in water or in a suitable organic solvent with a reagent such as acryloyl chloride, DVS or derivatives thereof to introduce an activated carbon-carbon double bond onto the surface of said silica nanoparticles.

The attachment of thrombin molecules to the nanoparticles having reactive chemicals groups on their surface may be accomplished chemically, by allowing said thrombin molecules to form covalent bonds either directly with said reactive groups, or with a suitable spacer arm that is bonded to said reactive groups.

According to one preferred embodiment of the invention, the direct covalent binding of thrombin to the nanoparticles is most preferably carried out by allowing the primary amine groups of the thrombin molecules to react either with the activated double bonds provided on the surface of the nanoparticles via a Michael addition reaction, or with the aldehyde groups provided on said surface through the formation of Schiff Bases. In general, preferred reaction conditions include suspending the nanoparticles having either activated double bonds or aldehyde groups on their surface in a suitable solvent, which is most preferably water, under alkaline pH, and adding thereto thrombin molecules such that the weight ratio between said nanoparticles and said thrombin molecules is preferably in the range of 100:1 to 5:1, following which the reaction mixture is shaken at room temperature for a period of time ranging from 30 minutes to several hours. Subsequently, residual activated double bonds or aldehyde groups are blocked using appropriate reagents, such as glycine, ethanolamine or other amino containing compounds, and the thrombin-conjugated nanoparticles are isolated from the reaction mixture using conventional separation techniques, such as centrifugation or magnetic separation methods, if applicable. Hereinafter, thrombin conjugated nanoparticles having thrombin molecules directly covalently bonded to reactive groups provided on the surface of the nanoparticles are designated X-Thr, wherein X identifies the nanoparticles (e.g., X is Mag, AB or $SiO_2$) and Thr indicates thrombin.

According to another preferred embodiment of the invention, a suitable spacer arm is covalently linked to the reactive groups provided on the surface of the nanoparticles, following which the thrombin molecules are caused to form chemical bonds with said spacer arm. A suitable spacer arm is most preferably a molecule having at least two functional groups, which may be identical or different, wherein the first functional group is capable of forming a covalent bond with the reactive chemical groups provided on the surface of the nanoparticles, and the second functional group is capable of subsequently forming a covalent bond with the thrombin molecules.

A particularly preferred molecule that may be used as a spacer arm according to the present invention has a first functional group which is a primary amine group, that may either undergo a Michael addition or form a Schiff base with the activated double bonds or the aldehyde groups provided on the nanoparticles, respectively, under the conditions described hereinabove for the reactions between the various nanoparticles and thrombin, and a second functional group capable of participating in a subsequent chemical reaction with reactive groups of the thrombin molecules. Preferably, the second functional group of the spacer arm is a carboxylate group, such that the covalent binding of the thrombin to the spacer arm may be accomplished via the carboiimide activation method, according to the reaction conditions that are as described by Melamed and Margel [J. of Colloid and Interface Science 241, 357 (2001)], which is incorporated herein by reference. Alternatively, the spacer arm may have a second functional group that is selected from among primary amine, aldehyde, carbon-carbon double bonds and hydroxyl. It may be readily appreciated that in the case wherein the first and second functional groups of the spacer arm are identical (for example, both groups are primary amine groups), then an excess of said spacer arm should be used in the reaction with the nanoparticles.

Preferred molecules that may be used as spacer arms are selected from the group consisting of BSA (bovine serum albumine), glutaraldehyde and 1-amino hexanoic acid. Hereinafter, thrombin conjugated nanoparticles wherein a spacer arm is covalently linked to reactive groups provided on the surface of the nanoparticles, with the thrombin molecules forming covalent bonds with said spacer arm are sometimes designated X-Spacer-Thr, wherein X identifies the nanoparticle (e.g., Mag, AB or $SiO_2$), Spacer identifies the molecule used as a spacer arm (e.g., BSA) and Thr indicates thrombin.

In another aspect, the present invention encompasses thrombin conjugated nanoparticles, wherein the thrombin molecules are physically adsorbed onto spacer arms, and wherein said spacer arms are covalently-linked to the surface of the nanoparticles. The attachment of the thrombin molecules to the nanoparticles is accomplished by causing said thrombin molecules to become physically adsorbed onto a suitable spacer arm that is bonded to the reactive groups provided on the surface of the nanoparticles. A spacer arm which is capable of strongly attracting thrombin through physical adsorption is most preferably albumin. Typically, following the introduction of the spacer arm onto the surface of the nanoparticles utilizing the synthetic procedures described above, the nanoparticles having the spacer arm covalently linked thereto are suspended in an alkaline aqueous solution, the pH of said solution being in the range of 7 to 9, at a temperature not higher than 37° C., following which thrombin is added to the suspension, such that the weight ratio thrombin:nanoparticles is preferably in the range of 1:100 to 1:5, to obtain the desired thrombin-conjugated nanoparticles. Hereinafter, thrombin conjugated nanoparticles that are based on the physical binding of thrombin to the nanoparticles through a spacer arm are sometimes labeled as follows: X~Thr, wherein X identifies the nanoparticle (e.g., Mag, AB, $SiO_2$, etc).

The thrombin-conjugated nanoparticles according to the invention have useful therapeutic properties in the treatment and/or prophylaxis of conditions associated with the blood clotting process.

More specifically, the thrombin-conjugated nanoparticles according to the present invention allow rapid and effective interaction of thrombin with fibrinogen in aqueous solution, plasma and blood, to form the desired fibrin clot, said clot being characterized by the presence of nanoparticles entrapped within its polymeric network.

It has been found that the thrombin conjugated to the nanoparticles according to the present invention possesses different properties from those of the free enzyme, i.e. different clotting time, and significantly increased stability towards various potentially disruptive conditions, e.g. inhibitors, bacteria, increased temperature, storage time, pH, light, lyophilization, etc. The fibrin sealant formed with the thrombin-conjugated nanoparticles of the present invention is also safer than the sealant formed with free thrombin, particularly for allergic patients, since no significant leaching of free thrombin from the conjugated nanoparticles is prevented. Under similar thrombin concentrations, the clotting time with fibrinogen of the physically-adsorbed thrombin nanoparticles was shorter than that of the covalently bonded thrombin nanoparticles. Also, under similar thrombin concentrations, the clotting time of the thrombin conjugated nanoparticles was according to the following order: blood<plasma<aqueous solution. An opposite behavior was observed for the free enzyme, i.e. plasma<blood. A significant acceleration in the clotting time of the thrombin-conjugated nanoparticles was observed by adding $CaCl_2$ to the conjugated nanoparticles-containing aqueous suspension. A similar acceleration effect of $CaCl_2$ was observed for the free enzyme, but significantly more moderate. A moderate acceleration in the clotting time of both the free and immobilized thrombin was also observed by adding factor XIII to the thrombin or thrombin-conjugated nanoparticles containing aqueous suspension.

Accordingly, the present invention provides the thrombin-conjugated nanoparticles for use as a therapeutic substance. More particularly, the present invention provides the thrombin-conjugated nanoparticles for use in the treatment of conditions associated with blood clotting process.

In a further aspect, the present invention provides a therapeutic composition comprising thrombin-conjugated nanoparticles together with a suitable carrier for treating conditions associated with blood clotting process. It should be noted that the therapeutic composition according to the present invention may be either in a solid form or in a liquid form.

According to one preferred embodiment, the thrombin-conjugated nanoparticles will be provided in a therapeutic composition in the form of a solid, dry powder that is suitable for topical administration to the desired body site. It has been found that a particularly stable composition comprising dried thrombin-conjugated nanoparticles may be obtained by lyophilization of an aqueous suspension of the thrombin-conjugated nanoparticles in the presence of one or more suitable dispersants or surfactants, such as gelatin or polyvinylpyrrolidone, gelatin being most preferred. According to a particularly preferred embodiment, the weight ratio between the thrombin-conjugated nanoparticles and the gelatin in the aqueous suspension before the lyophilization is in the range of 1:2 to 2:1. Accordingly, a solid therapeutic composition comprising dried thrombin-conjugated nanoparticles and at least one dispersant, which is most preferably gelatin, forms another aspect of the present invention. The dried thrombin-conjugated nanoparticles can be stored at 4° C. or at room temperature for at least 6 months without significant loss of their clotting time with fibrinogen.

In another preferred embodiment of the present invention, the thrombin-conjugated nanoparticles are provided in the form of a solid dry powder supported on a suitable carrier such as cellulose, collagen or gelatin sheets. For example, covering a sheet of collagen with the thrombin-conjugated aqueous suspension and subsequently lyophilizing the same will give the desired supported nanoparticles.

According to another preferred embodiment, the thrombin-conjugated nanoparticles will be provided in a therapeutic composition that is in a liquid form. To this end, thrombin-conjugated nanoparticles of the present invention per se, or thrombin-conjugated nanoparticles obtained following lyophilization in the presence of gelatin, as described above, may be re-suspended in a suitable liquid vehicle, which is most preferably water, in a weight concentration ranging between 0.01 to 5%. The diameter of the dispersed thrombin conjugated nanoparticles is similar to the diameter of the nanoparticles before lyophilization.

It should be noted that suitable additives, such as Ca salts (e.g., $CaCl_2$), factor XIII and antifibrinolytic agents such as aprotinin or tranexamic acid may be present in the aforementioned therapeutic compositions of the present invention. These additives may be introduced to the aqueous suspension containing the thrombin-conjugated nanoparticles and (optionally) the dispersant prior to the lyophilization.

The thrombin-conjugated nanoparticles of the present invention may be used, or adapted for use, in connection with a very broad range of clinical conditions and situations. Thus, the thrombin-conjugated nanoparticles disclosed and claimed herein may be used to assist normal hemostasis, induce hemostasis in hemophilia patients and to cause accelerated wound healing. In addition, they may be employed in circumstances requiring the use of a tissue glue (for example, in the anchoring of medical devices to living tissue). Finally, the thrombin-conjugated nanoparticles may be used in many, if not all, areas of surgical practice, including general surgery, orthopedics, urology, plastic surgery, gynecology, dental surgery, circumcision and cardiovascular surgery. The stability of the presently-claimed nanoparticles, together with their relative simplicity of use, renders them suitable for use in the aforementioned clinical indications in a wide range of different settings including in the armed services (e.g. in field hospitals and on the battlefield), home care, inpatient and outpatient clinics and operating suites, as well as in various industrial settings.

Accordingly, the present invention provides a method for preparing fibrin-containing biological sealant, wherein said method comprises contacting fibrinogen with a therapeutically effective amount of thrombin-conjugated nanoparticles of the present invention. Preferably, the fibrinogen is contacted with a dry powder comprising thrombin-conjugated nanoparticles and a dispersant, wherein said dispersant is most preferably gelatin, in a liquid medium selected from the group consisting of aqueous solution, plasma or blood, whereby the fibrin sealant is formed. Most preferably, the thrombin-conjugated nanoparticles and fibrinogen are contacted in the presence of calcium ions or factor XIII.

The presently-claimed thrombin-conjugated nanoparticles are intended for use in the context of enhanced blood clotting and wound closure and repair, all of which are surface phenomena. Consequently, the therapeutically-effective amount of the thrombin-conjugated nanoparticles to be used in the above-defined method, and in the preparation of the above-defined therapeutical composition, is to be understood as an amount appropriate for the surface area of the wound to be treated. In practice, this means that the user will select an amount of the nanoparticle preparation that is sufficient to either partially cover or fully cover the wound area.

It should be noted that the thrombin-conjugated nanoparticles of the present invention may also be used for additional purposes, e.g. controlled release by encapsulation or surface binding of an appropriate drug (e.g. antibiotics) or for targeting by binding to the surface in addition to thrombin an homing reagent. To this end, thrombin was bound covalently or physically to nanoparticles containing encapsulated antibiotics, e.g. Ampicillin, by using similar procedures to that described above, substituting the nanoparticles for nanoparticles containing the encapsulated Ampicillin.

Homing agents, e.g. Ampicillin, for targeting was bound to the nanoparticles by using similar procedures to that described above, substituting the blocking step of residual activating groups (after completing the thrombin binding) with glycine for the binding of the homing agent.

EXAMPLES

1. Materials and Methods

1-A. Materials

All reagents used in this work were of analytical grade from commercial sources. Thrombin (from bovine plasma, 50 U/mg)) was purchased from Merck; Antithrombin III (from bovine plasma), Fibrinogen (fraction I, type I-S from bovine plasma), Gelatin 60 and 300 from porcine skin, Human serum albumin (HSA), Bovine serum albumin (BSA) and Ampicillin sodium salt were purchased from Sigma; Factor XIII (Fibrogammin P, 3.4 U/mg) was purchased from Aventis Behring GmbH, Germany; D-Phenylalanyl-L-pipecolyl-L-arginine-p-nitroanilide dihydrochloride (S-2238, a substrate for thrombin) was purchased from Chromogenix, Sweden; Plasma (human normal control plasma) was purchased from Diagnostica STAGO, France. Water was purified by passing deionized water through an Elgastat Spectrum reverse osmosis system (Elga Ltd., High Wycombe, UK).

1-B. Diameter and Size Distribution

The diameter and size distribution of the various nanoparticles were determined by scanning electron microscopy and transmission electron microscopy (JSM-840, Jeol), and submicron and micron size particle analyzers of Coulters Electronics, UK.

1-C. Blood Clotting Measurements

Blood clotting measurements in fibrinogen solution, plasma and blood of thrombin and thrombin immobilized to the various nanoparticles were performed with the STart-4 equipment supplied by Diagnostica Stago, France. The reported clotting time values are an average of at least 4 measurements of each type of Thr-immobilized nanoparticles.

1-D. Sterilization of the Thrombin Mag Conjugated Nanoparticles

Sterilization of the Mag nanoparticles coated with dextran and activated with divinyl sulfone was performed by means of the following two steps: (1) passing the nanoparticle aqueous suspension through 0.2 μm filter paper; (2) sterilizing the nanoparticle suspension with a standard autoclave at high pressure and 120° C. for 20 min. The magnetic columns as well as the other necessary tools were also sterilized by autoclaving. The binding of the BSA was then performed in a laminar hood under sterile conditions. The sterilized nanoparticle suspension (in 0.1M PBS) was then dispensed (in 100 μl aliquots) into small vials. These vials were then either stored at 4° C. or their contents lyophilized, until required for use.

1-E. Measuring the Amount of Bound Thrombin

The amount of bound thrombin was determined with the thrombin substrate chromogenix reagent S-2238. Briefly, 1.9 ml of 0.1M Tris buffer at pH 8.3 were added to 0.2 ml aqueous suspension of the thrombin-conjugated nanoparticles. Then, 0.1 ml of the reagent S-2238 were added. The tube was then shaken for 2 min at room temperature. Thereafter, the supernatant of the nanoparticle suspension was separated from the nanoparticles themselves by centrifugation, ultrafiltration or magnetic separation. The absorption of the supernatant at 405 nm was then measured. The amount of thrombin conjugated to the various nanoparticles was determined according to the supernatant absorption intensity at 405 nm, according to a calibration curve of known concentrations of free thrombin.

Preparation 1

Synthesis of Iron Oxide-Containing Nanoparticles and Surface Modification Thereof Synthesis 10 ml of deairated aqueous solution containing 10 mg gelatin (300 bloom) and 0.07 mmol $FeCl_2.4H_2O$ was shaken at 60° C. for 10 min. 0.014 mmol $NaNO_2$ was added to the solution, and after 10 min the pH of the solution was increased to 9.5 by the addition of 0.3M NaOH solution. The solution was shaken for another 40 min. Thereafter, the procedure of the successive addition of $FeCl_2.4H_2O$ $NaNO_2$ and NaOH to pH 9.5 was repeated three times. The formed magnetic nanoparticles were then cleaned from excess reagents by the use of magnetic columns. Transmission Electron Microscopy studies and coulter measurements demonstrated that the average diameter of the dried Mag nanoparticles is 20 nm±10% and the hydrodynamic average diameter of these Mag nanoparticles dispersed in water is 70 nm±10%.

Mag nanoparticles containing encapsulated antibiotics such as Ampicillin sodium salt were prepared by using a similar procedure, in which the aforementioned 10 ml aqueous solution containing 10 mg gelatin was substituted by a 10 ml aqueous solution containing 2 mg Ampicillin sodium salt and 10 mg gelatin.

Surface Modification

The Mag nanoparticles (20 nm average dry diameter) obtained according to the procedure described above were shaken in water at 85° C. in the presence of 2% (w/v) dextran (MW 37,5000) for 1 h, to form a suspension, which was allowed to cool to room temperature. The dextran-coated nanoparticles were then washed from excess dextran by magnetic columns. 0.66 ml DVS was then added into a 40 ml aqueous suspension containing 100 mg of the washed dextran coated Mag nanoparticles at 60° C. Thereafter, triethyl amine was added gradually to the nanoparticle suspension, until the pH reached pH 10.5. The suspension was then shaken at 60° C. for approximately 12 h. Excess DVS was then washed from the modified nanoparticles by means of magnetic columns. The modified Mag nanoparticle aqueous suspension was then stored at 4° C.

Modification of the surface of the Ampicillin encapsulated Mag nanoparticles was performed similarly, substituting the Mag nanoparticles with Ampicillin encapsulated Mag nanoparticles.

Preparation 2

Synthesis of Albumin Nanoparticles and Surface Modification Thereof

Synthesis

An aqueous solution (25 ml) containing 1 g human serum albumin was shaken at room temperature for 15 minutes, following which 50 ml of n-propanol were added thereto, to obtain particles of 0.7-1.5 μm diameter. The temperature was then raised to 50° C. for 15 min, and then to 82° C. (the boiling point of n-propanol) for 1 h. The AB nanoparticles were then washed extensively by several centrifugation cycles in aqueous solution.

AB nanoparticles containing encapsulated antibiotics such as Ampicillin sodium salt were prepared by using a procedure similar to that described above, substituting the 25 ml aqueous solution containing 1 g human serum albumin with a 25 ml aqueous solution containing 2 mg Ampicillin sodium salt and 1 g human serum albumin.

Surface Modification 4 ml of glutaraldehyde 25% were added to 100 ml of pure water containing 1 g of dispersed AB particles obtained according to the procedure described above. The suspension was then shaken at room temperature for 3 h. The resulting nanoparticles were then washed extensively from excess glutaraldehyde by several centrifugation cycles in pure water, and then stored at 4° C.

Modification of the Ampicillin encapsulated AB nanoparticles was performed similarly, by substituting the AB nanoparticles with Ampicillin encapsulated AB nanoparticles.

Preparation 3

Synthesis of Silica Nanoparticles Deposited on an Organic (Polystyrene) Core and Surface Modification Thereof Synthesis Polystyrene particles of 2.3 μm±10% (1 g) were added to a flask containing ethanol (93.6 ml) and distilled water (1.9 ml), and the mixture was sonicated to disperse the particles. Ammonium hydroxide (1.3 ml) and $Si(OEt)_4$ (3.2 ml) were then added, and the suspension was shaken at room temperature for 12 h. The resulting $SiO_2$ coated polystyrene nanoparticles were freed from free silica nanoparticles (ca. 30 nm diameter) by repeated centrifugation cycles. The $SiO_2$ coated polystyrene nanoparticles were then dried in a vacuum oven. The content of the silica coating on the polystyrene particles was increased by repeating the aforesaid coating procedure. The silica content of the core-shell particles was 7.8% and 13.8% (w/w) after the first and second coating cycles, respectively. Scanning electron micrographs and cross sectional transmission electron micrographs demonstrated the complete coverage of the polystyrene core particles with a few layers of silica nanoparticles of approximately 30 nm average diameter.

Surface Modification

Dry $SiO_2$ coated polystyrene nanoparticles having an average size of 2.3 μl (100 mg) were introduced into a triple-neck flask containing 80 ml 0.1 M acetate buffer, pH 5.5. The mixture was then sonicated in order to disperse the particles, following which 0.4 ml of the amphiphile $Si(OEt)_3(CH_2)_3NH_2$ was added to the suspended particles. The suspension was then mechanically stirred at 60° C. for 12 h. Thereafter, the derivatized particles were washed by a few centrifugation cycles in acetate buffer, and then in distilled water. The resulting $SiO_2$ coated polystyrene nanoparticles, bearing amino groups on their surface were dispersed in water and stored at 4° C. prior to use.

The aforementioned $SiO_2$ coated polystyrene nanoparticles, having amino groups provided on their surface (300 mg) were introduced into a flask containing 10 ml bicarbonate buffer, 0.1 M at pH 8.3. The mixture was then sonicated in order to disperse the particles. 0.1 ml acryloyl chloride was then added to the suspension. The suspension was shaken at room temperature for 1 h. Excess acryloyl chloride was removed by a few centrifugation cycles in water. The resulting particles ($SiO_2$ coated polystyrene nanoparticles having activated double bonds on their surface) were dispersed in water and then stored at 4° C. prior to use.

Preparation 4

Synthesis of Silica Nanoparticles Deposited on an Organic (Polystyrene) Core, Having a Magnetic Layer Interposed Therebetween, and Surface Modification Thereof Polystyrene nanoparticles of average size 2.3 μm (1 g) were added to a flask containing 20 ml distilled water, following which the mixture was sonicated for a few minutes and then mechanically stirred at ca. 200 rpm. The temperature was then preset to 60° C. Nitrogen was bubbled through the suspension during the coating process to exclude air. 0.1 ml of iron chloride tetrahydrate aqueous solution (1.2 mmol in 10 ml $H_2O$) and 0.1 ml of sodium nitrite aqueous solution (0.02 mmol in 10 ml $H_2O$) were then successively introduced into the reaction flask. Thereafter, a sodium hydroxide aqueous solution (0.5 mmol in 10 ml $H_2O$) was added until a pH of ca. 10 was reached. This procedure was repeated four times. During this coating process the core polystyrene nanoparticles became brown-black colored. The suspension was then cooled to room temperature. The formed magnetic polystyrene particles were then washed extensively in water with a magnet and dried in a vacuum oven. The magnetic polystyrene particles were coated with silica nanoparticles (ca. 30 nm), according to the procedure described in preparation 3.

Surface Modification

The introduction of reactive chemical groups onto the surface of the magnetic $SiO_2$ coated polystyrene nanoparticles was accomplished similarly to the procedure of preparation 3.

Preparation 5

Synthesis of Silica Nanoparticles of 10-100 nm Diameter and Surface Modification Thereof Synthesis The following reagents were successively added into a flask: ethanol (93.6 ml), distilled water (1.5 ml), ammonium hydroxide (1.3 ml) and $Si(OEt)_4$ (2.8 ml). The resulting solution was then shaken at room temperature for ca. 5 h. The formed nanoparticles were washed by evaporation of the unreacted monomer, ethanol and ammonia. Water was added during the evaporation to retain the total volume of the silica suspension. The particles obtained were of ca. 10 nm±15% diameter.

Surface Modification

The introduction of reactive chemical groups onto the surface of the silica nanoparticles having diameter of approximately 10 nm was accomplished similarly to the procedure of preparation 3, with the following changes:

At the stage of introducing the primary amine groups, the buffer acetate at pH 5.5 was replaced with buffered water at pH 9.5, and the subsequent centrifugation was substituted with dialysis against water.

At the stage of introducing the double bond groups, centrifugation was substituted with dialysis against water.

Preparation 6

Covalent Binding of a Spacer Arm (Bovine Serum Albumin (BSA)) to Nanoparticles having Activated Double Bonds or Aldehyde Groups on their Surface BSA (10 mg) was added to vials containing 100 mg nanoparticles having either activated double bonds or aldehyde groups on their surface (obtained according to any of the preparations described above), suspended in 40 ml 0.1M bicarbonate buffer at pH 8.3. The suspension was shaken at room temperature for ca. 12 hours. Blocking of residual chemically reactive groups (activated double bonds or aldehydes) of the BSA conjugated particles was then performed by adding 400 mg glycine to each vial. The particle suspension was then shaken at room temperature for additional 2 hours, following which the BSA-conjugated nanoparticles were separated from excess BSA and glycine by centrifugation cycles or magnetic separation with 0.1M PBS (pH 7.4). The BSA-conjugated nanoparticles were then stored at 4° C. up. The amount of BSA bound to the various nanoparticles was measured according to Lowry method [J. Biol. Chem. 1951, 193, 265.]

Preparation 7

Direct Chemical Binding of Thrombin to Nanoparticles Having Activated Double Bonds or Aldehyde Groups on Their Surface The direct covalent binding of thrombin to nanoparticles having either activated double bonds or aldehyde groups on their surface (obtained according to preparations 1 to 5 described above) was accomplished similarly to the procedure of preparation 6, by replacing BSA with thrombin.

Preparation 8

Chemical Binding of Thrombin to Nanoparticles Through a BSA Spacer 123 mg NHS (Acetic acid N-hydroxysuccinimide ester) and 82 mg CMC (1-Cyclohexyl-3-(2-morpholinoethyl) carbodiimide metho-p-toluenesulfonate) were added to a suspension containing 100 mg nanoparticles conjugated with BSA (prepared according to preparation 6) suspended in 40 ml 0.1M phosphate buffer at pH 6.5. The nanoparticles suspension was then shaken at room temperature for 4 h. The activated conjugated nanoparticles were then separated from excess activating reagents by centrifugation cycles or magnetic separation with 0.1M PBS (pH—7.4). 10 mg thrombin was then added to the washed suspension, following which the suspension was shaken at room temperature for ca. 12 h. Blocking of residual activating groups was accomplished by adding 400 mg glycine to the nanoparticle suspension, and then shaking the suspension at room temperature for an additional 3 h. The thrombin-conjugated nanoparticles were then washed from unbound thrombin and glycine by means of either several cycles of centrifugation or magnetic separation with 0.1M PBS (pH—7.4). The thrombin-conjugated nanoparticles were then lyophilized or stored at 4° C. prior to use. The amount of thrombin conjugated to the nanoparticles was determined with the chromogenix reagent S-2238, according to the description given hereinabove.

Preparation 9

Physical Binding of Thrombin to Nanoparticles Having BSA Spacers 5 mg thrombin were added to a 0.1M PBS (pH 7.4) suspension containing 100 mg BSA-conjugated nanoparticles (that were prepared according to preparation 6 above). The suspension was then shaken at room temperature for ca. 12 h. The thrombin-conjugated nanoparticles were then washed from unbound thrombin by centrifugation cycles or magnetic separation with 0.1M PBS (pH—7.4). The thrombin-conjugated nanoparticles were then lyophilized or stored at 4° C. prior to use. The amount of thrombin-conjugated to the nanoparticles was determined with the chromogenix reagent S-2238, according to the description given hereinabove.

Example 1

Extent of Leakage of Thrombin (Thr) Immobilized to Various Nanoparticles Suspended in PBS in the Absence or Presence of 4% Human Serum Albumin (HSA)

Vials containing nanoparticles bonded with 37 µg Thr suspended in 120 µl 0.1 M PBS (pH=7.4) in the absence or presence of 4% HSA were shaken at room temperature. At various time intervals the Thr immobilized particles were removed from the supernatants. The amount of leached Thr in the supernatants was then measured as described in the foregoing experimental section. The results are indicated in Table 1.

TABLE 1

Extent of leakage of Thr immobilized to various nanoparticles suspended in PBS in the absence (A) or presence (B) of 4% HSA.

| Thrombin-conjugated | Leached Thr (%) Time (h) | | |
|---|---|---|---|
| nanoparticle | 0.30 | 4 | 24 |
| A | | | |
| Mag~Thr | 0 | 0.07 | 0.13 |
| AB~Thr | 0 | 0 | 0 |
| SiO$_2$~Thr (2.3 µm) | 1.9 | 6.4 | 11.2 |
| B | | | |
| Mag~Thr | 0 | 1.9 | 6.5 |
| AB~Thr | 0 | 0 | 0 |
| SiO$_2$~Thr (2.3 µm) | 2.4 | 11.4 | 16.5 |

The results shown in Table 1 indicate that there was no leakage of Thr to PBS, or PBS containing 4% HSA, from Thr immobilized to AB nanoparticles suspended in PBS. Table 1 also shows that the extent of leakage of Thr from Thr immobilized to Mag nanoparticles suspended in PBS is very small, i.e. after 0.5 h no leakage was detected; after 4 h, 0.07% and 1.9% of Thr was leached to PBS and PBS containing 4% HSA, respectively. The highest degree of leakage of Thr was observed for SiO$_2$~Thr, i.e. after 0.5 h 1.9% and 2.4% of Thr was leached to PBS and PBS containing 4% HSA, respectively. It should however be noted that usually the realistic clotting time in plasma, or blood, of the Thr immobilized nanoparticles is less than 1 min, and in that period of time the extent of leached Thr to PBS containing 4% HSA was negligible (less than 0.3%). It should also be noted that for the covalent Thr-bonded nanoparticles no leakage was detected even after 24 h.

In all the experiments described above the clotting times in plasma of the supernatants removed from the nanoparticles were also tested. However, plasma clotting was not observed up to 500 seconds, at which time the experiments were terminated.

Example 2

Effect of Diameter of the SiO$_2$ Nanoparticles on the Clotting Time in Plasma of SiO$_2$~Thr Suspended in PBS The clotting time was measured at 37° C. by mixing 50 µl plasma with samples containing 32 µg of Thr immobilized to SiO$_2$ nanoparticles of various diameters suspended in 100 µl 0.1M PBS (pH=7.4). The results are shown in the following table.

TABLE 2

Effect of the diameter of the SiO$_2$ nanoparticles on the clotting time in plasma of SiO$_2$~Thr suspended in PBS.

| Diameter (µm) | Particles (mg) | Bound Thr (µg) | Clotting time (sec) |
|---|---|---|---|
| 0.01 | 0.4 | 32 | 15.2 ± 0.3 |
| 0.75 | 3.9 | 32 | 32.3 ± 3.6 |
| 2.3 | 9.1 | 32 | 25.4 ± 2.5 |
| 3 | 11.4 | 32 | 23.6 ± 2.6 |
| 4.5 | 16.8 | 32 | 37.8 ± 2.7 |

Example 3

Figure 1B:
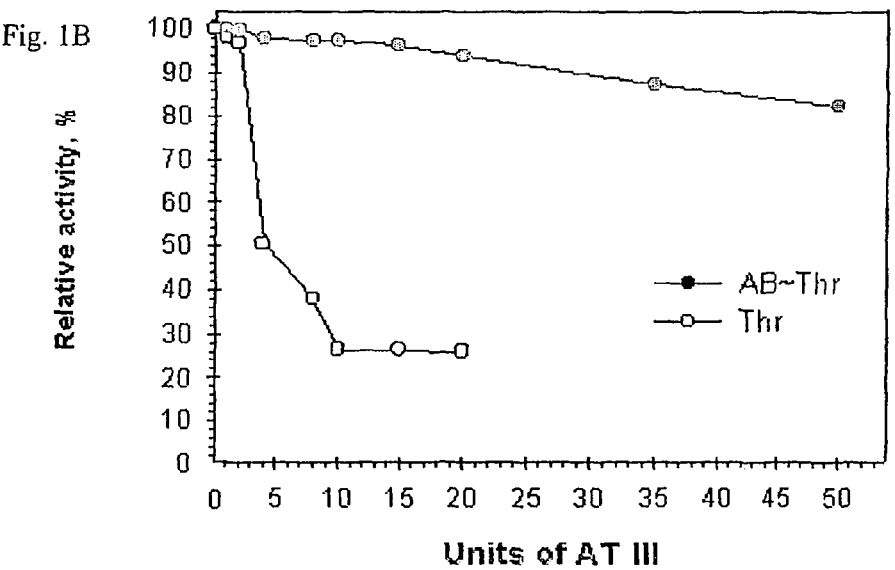
Figure 1C:
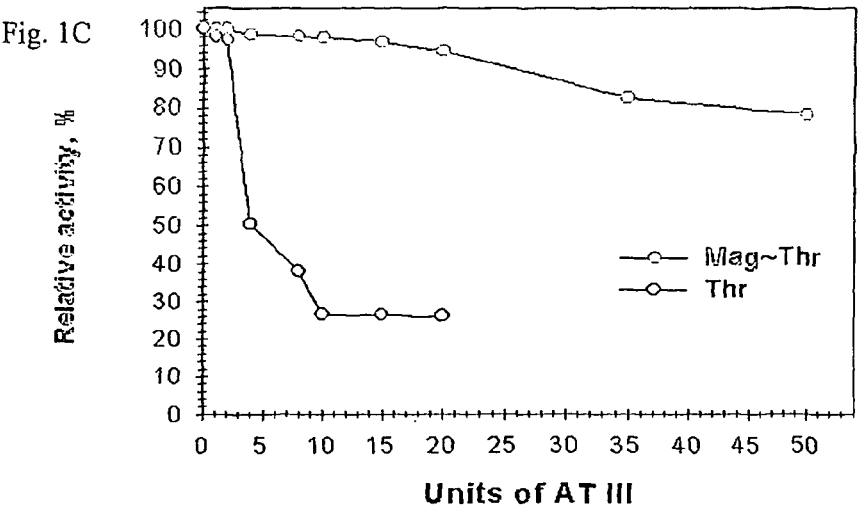

Effect of the inhibitor Antithrombin III on the activity of Thr and immobilized Thr: SiO$_2$~Thr (2.3 µm) (A), AB~Thr (B) and Mag~Thr (C) Suspended in PBS Vials containing 40 µg Thr or Thr bonded nanoparticles suspended in 200 µl 0.1 M PBS (pH=7.4) in the presence of different concentrations of Antithrombin III were shaken at RT for 1 h. The Thr immobilized particles were then removed from the supernatant. The remained activity of Thr and Thr bonded nanoparticles was then measured as described in the experimental part. FIG. 1 demonstrates the significant stabilization of Thr against inhibitors (e.g. antithrombin III) obtained by immobilizing the Thr to the various nanoparticles (SiO$_2$, AB and Mag). For example, in the presence of 5 units of antithrombin III, the free Thr lost about 75% of its original activity while Thr immobilized to Mag lost about 2% of its original activity.

Example 4

Effect of 8.3 mM CaCl$_2$ on the Clotting Time in Plasma and Blood of Thr and SiO$_2$~Thr (2.3 µm), AB~Thr and Mag~Thr ~Suspended in PBS Clotting time was measured at 37° C. by mixing 60 µl plasma (or blood) with samples containing, each sample, 13 µg of Thr or Thr immobilized to various nanoparticles suspended in 100 µl 0.1M PBS (pH=7.4) in the absence or presence of 8.3 mM CaCl$_2$. The results are shown table 3.

TABLE 3

Effect of 8.3 mM CaCl$_2$ on the clotting time in plasma and blood of Thr and SiO2~Thr (2.3 μm), AB~Thr and Mag~Thr suspended in PBS.

| Thrombin conjugated nanoparticle | CaCl$_2$ (mM) | Coagulation time in plasma (sec) | Coagulation time in blood (sec) |
|---|---|---|---|
| Mag~Thr | 0 | 47.4 ± 1.3 | 33.1 ± 1.3 |
| Mag~Thr | 8.3 | 19.7 ± 1.1 | 14.2 ± 1.3 |
| AB~Thr | 0 | 39.8 ± 2.7 | 27.8 ± 3.5 |
| AB~Thr | 8.3 | 17.5 ± 1.1 | 13.7 ± 3.2 |
| SiO$_2$~Thr | 0 | 60.7 ± 3.5 | 44.3 ± 2.3 |
| SiO$_2$~Thr | 8.3 | 31.1 ± 2.2 | 25.2 ± 2.2 |
| Thr | 0 | 21.5 ± 1.8 | 25.3 ± 2.1 |
| Thr | 8.3 | 12.3 ± 2.5 | 16.7 ± 2.5 |

Table 3 illustrates the following:

(1). The clotting time of Thr in plasma is shorter than in blood. Contrarily, the clotting time of the immobilized Thr nanoparticles in plasma is longer than in blood.

(2). Addition of 8.3 mM CaCl$_2$ to plasma or blood leads to decrease in the clotting time of both Thr and the immobilized Thr nanoparticles. However, this effect is significantly more prominent for the immobilized Thr nanoparticles than for the Thr.

(3). Under the described experimental conditions, the clotting times in blood containing additional 8.3 mM CaCl$_2$ and AB~Thr and Mag~Thr are shorter than that of Thr, i.e. 13.7, 14.2 and 16.7 sec., respectively.

Example 5

Clotting Time in Plasma as Function of Storage at RT of Thr and SiO$_2$~Thr Suspended in PBS Clotting time was measured at 37° C. by mixing 50 μl plasma with samples containing, each sample, 20 μg of Thr or Thr immobilized to SiO$_2$ nanoparticles (2.3 μm) suspended in 100 μl 0.1M PBS (pH=7.4). The results are shown in FIG. 2 (>600—Plasma clotting was not observed up to 600 seconds, at which time the experiment was terminated).

Figure 2:
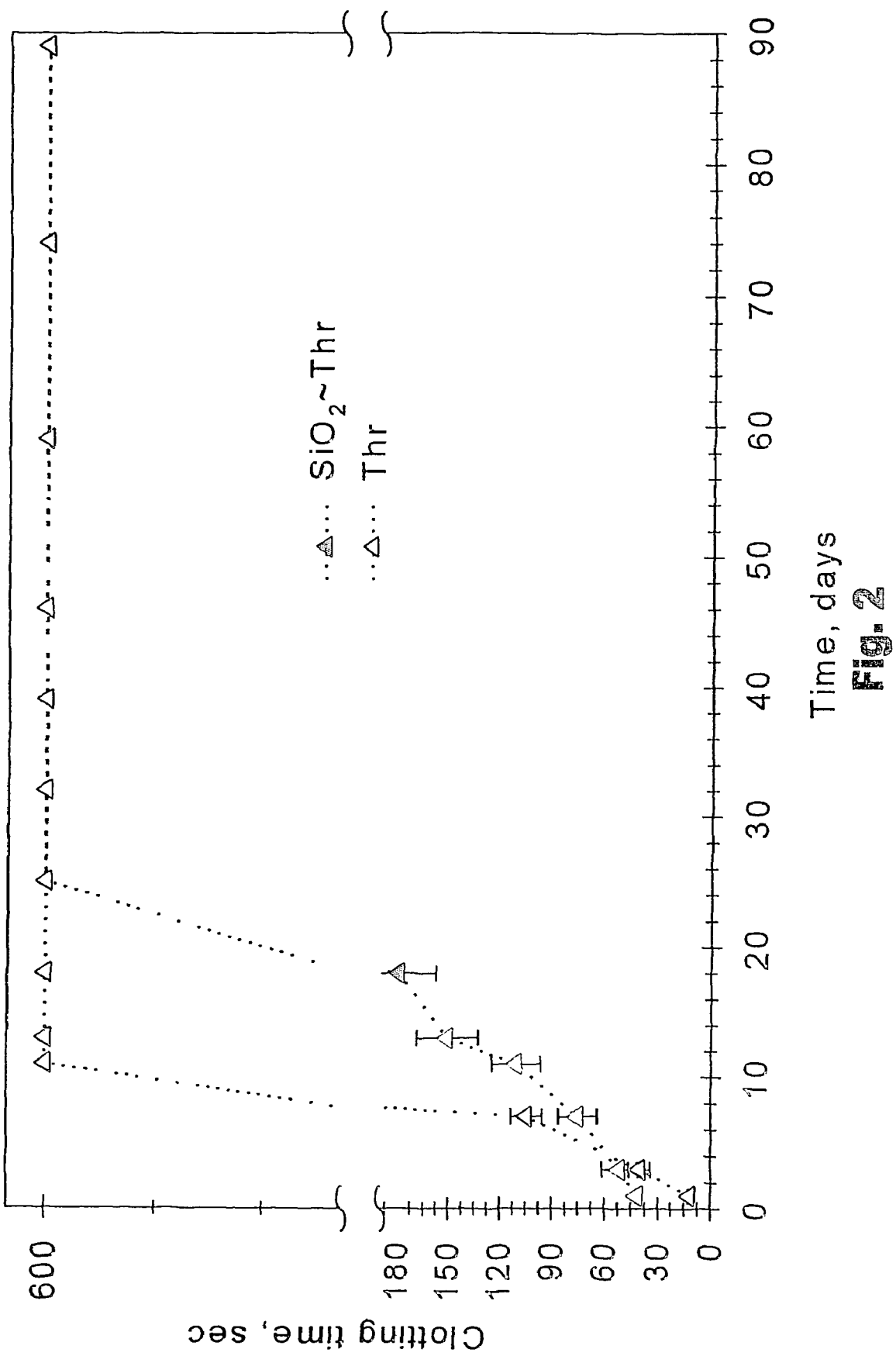
FIG. 2. Clotting time in plasma as a function of storage at RT of Thr and $SiO_2$~Thr suspended in PBS.

FIG. 2 demonstrates the storage stability at RT obtained by immobilizing Thr to SiO$_2$ nanoparticles (2.3 μm). For example, the clotting time in plasma of Thr and SiO2~Thr suspended in PBS and stored at RT for 8 days increased by ca. 14 and 1.8, respectively.

Example 6

Clotting Time in Plasma as a Function of Storage at Room Temperature of Thr and AB~Thr Suspended in PBS Clotting time was measured at 37° C. by mixing 50 μl plasma with samples containing, each sample, 20 μg of Thr or Thr immobilized to AB nanoparticles suspended in 100 μl 0.1M PBS (pH=7.4). The results are shown in FIG. 3.

Figure 3:
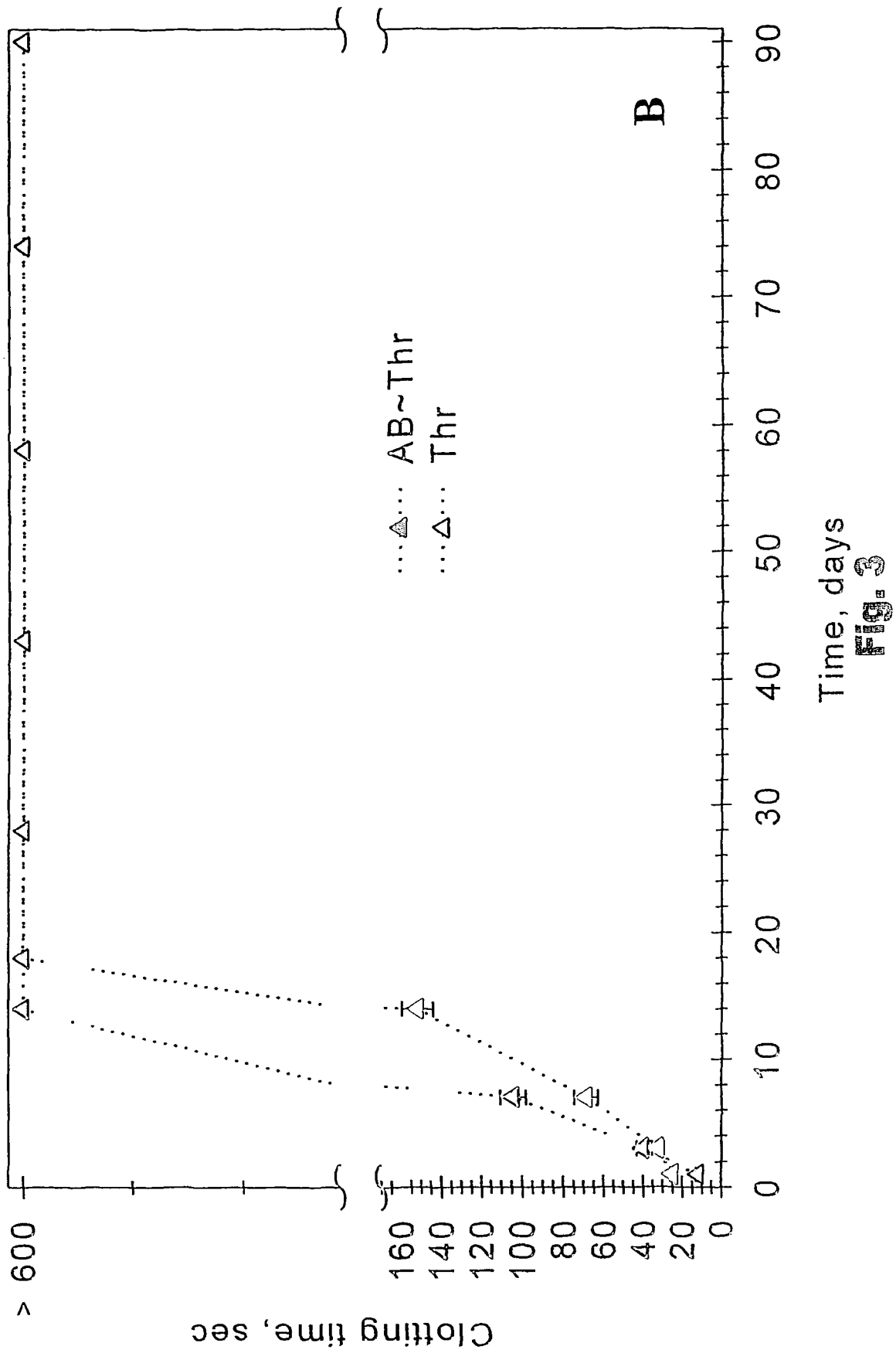
FIG. 3. Clotting time in plasma as a function of storage at RT of Thr and AB~Thr suspended in PBS.

FIG. 3 demonstrates the storage stability at RT obtained by immobilizing Thr to AB nanoparticles. For example, the clotting time in plasma of Thr and AB~Thr suspended in PBS and stored at RT for 8 days increased by ca. 11 and 2.3, respectively.

Example 7

Clotting Time in Plasma as a Function of Storage Time at RT of Thr and Mag~Thr Suspended in PBS Clotting time was measured at 37° C. by mixing 50 μl plasma with samples containing, each sample, 20 μg Thr or Thr immobilized to Mag nanopartilcles suspended in 100 μl 0.1M PBS (pH=7.4). The results are shown in FIG. 4.

Figure 4:
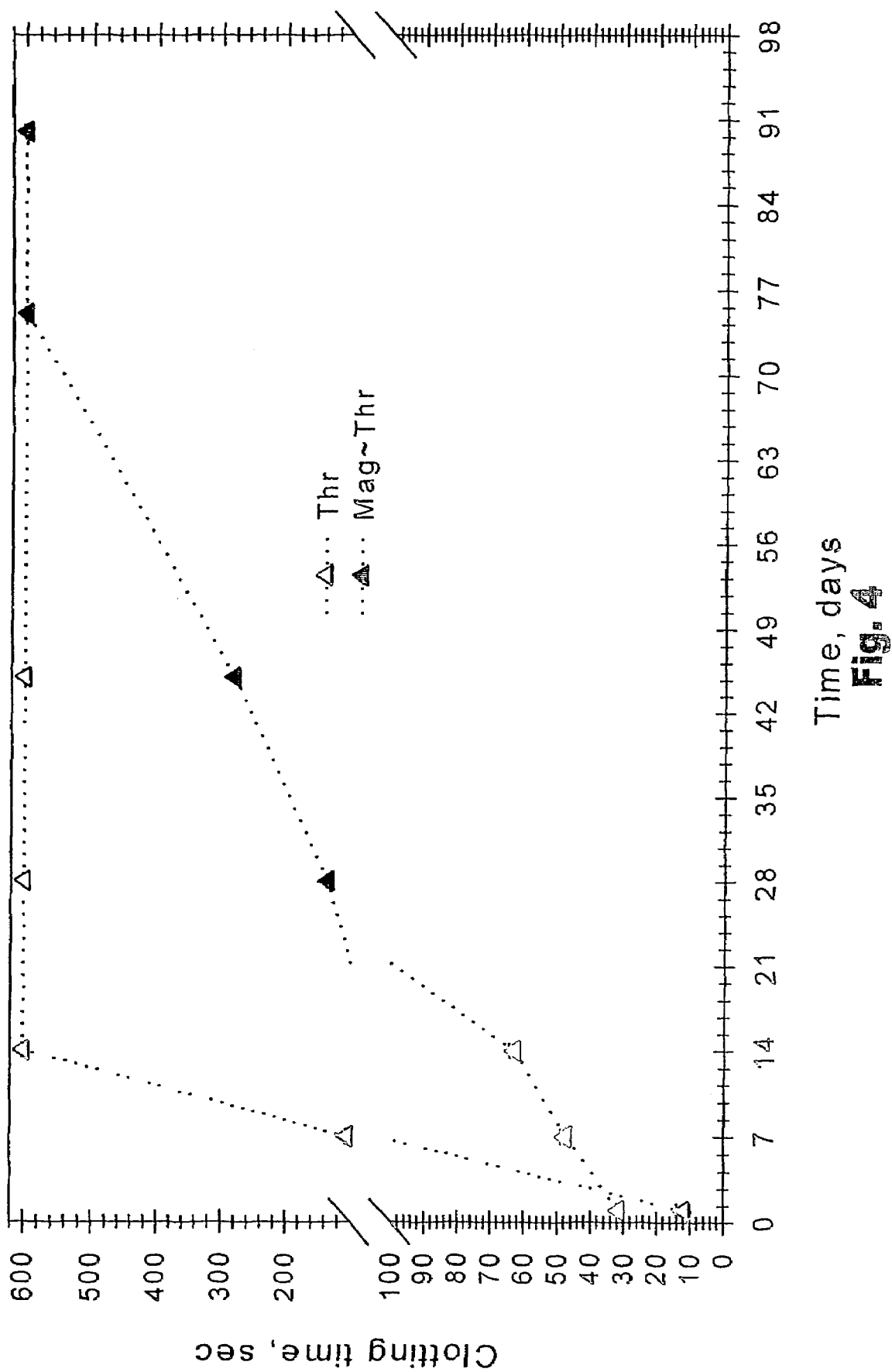
FIG. 4. Clotting time in plasma as a function of storage time at RT of Thr and Mag~Thr suspended in PBS.

FIG. 4 demonstrates the storage stability at RT obtained by immobilizing Thr to Mag nanoparticles. For example, the clotting time in plasma of Thr and Mag~Thr suspended in PBS and stored at RT for 7 days increased by ca. 12 and 1.4, respectively.

Example 8

Effect of Sterilization on the Clotting Time in Plasma of Thr and Mag~Thr Suspended in PBS and Stored at RT Clotting time was measured at 37° C. by mixing 50 μl plasma with samples containing, each sample, 20 μg sterilized or non-sterilized Thr or immobilized Thr suspended in 100 μl 0.1M PBS (pH=7.4). The results are shown in FIG. 5.

Figure 5:
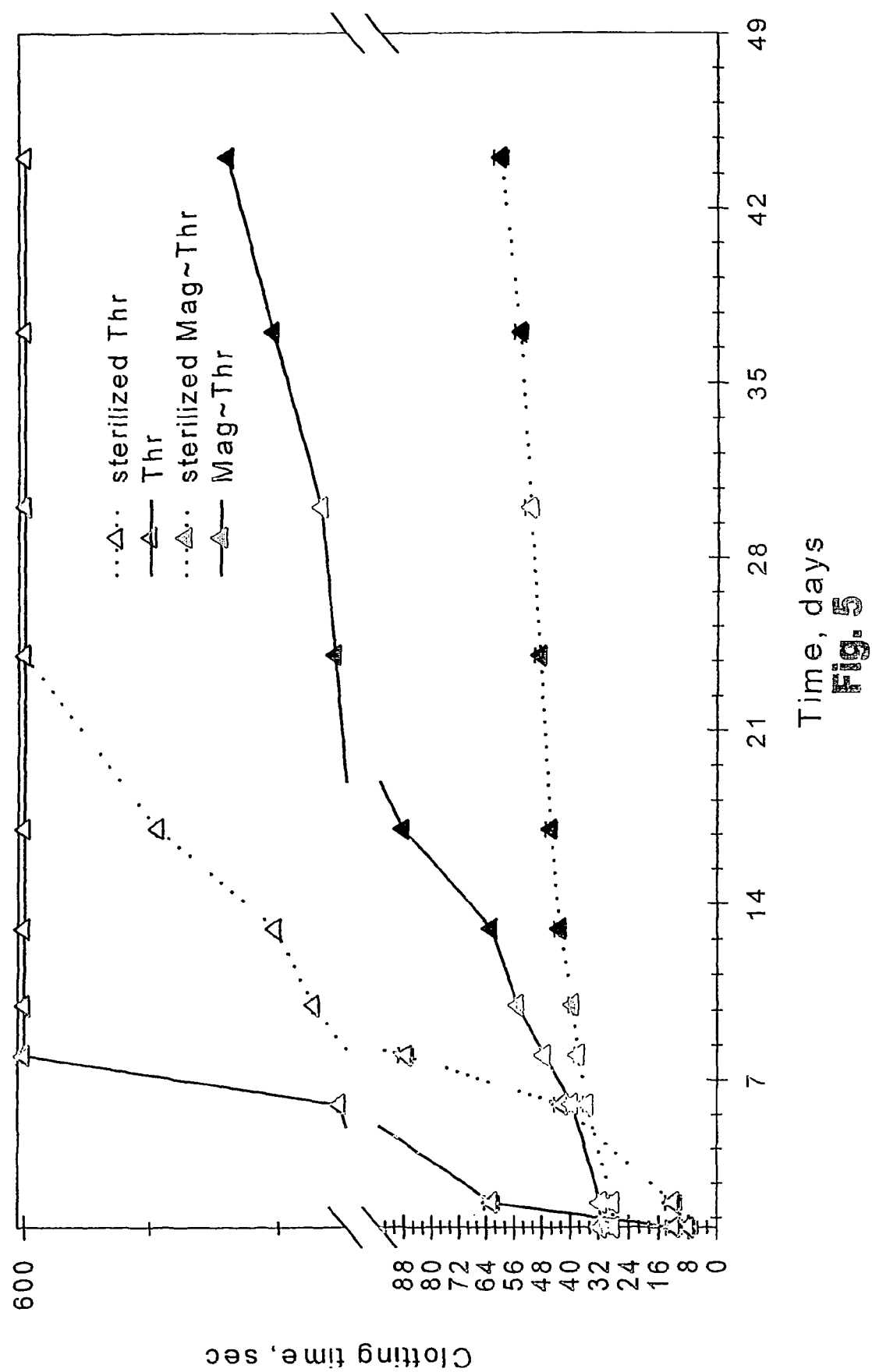
FIG. 5. Effect of sterilization on the clotting time in plasma of Thr and Mag~Thr suspended in PBS and stored RT.

FIG. 5 demonstrates the bacteria stability at RT obtained by immobilizing Thr to Mag nanoparticles (as shown by sterilizing the Thr and Mag~Thr suspension in PBS). For example, the clotting time in plasma of non-sterilized and sterilized Mag~Thr suspended in PBS and stored at RT for 14 days increased by ca. 1.7 and 1.3, respectively.

Example 9

Effect of Sterilization on the Clotting Time in Blood of Thr and Mag~Thr Suspended in PBS and Stored at RT Clotting time was measured at 37° C. by mixing 50 μl blood with samples containing, each sample, 20 μg sterilized Thr or immobilized Thr suspended in 100 μl 0.1M PBS (pH=7.4). The results are shown in FIG. 6.

Figure 6:
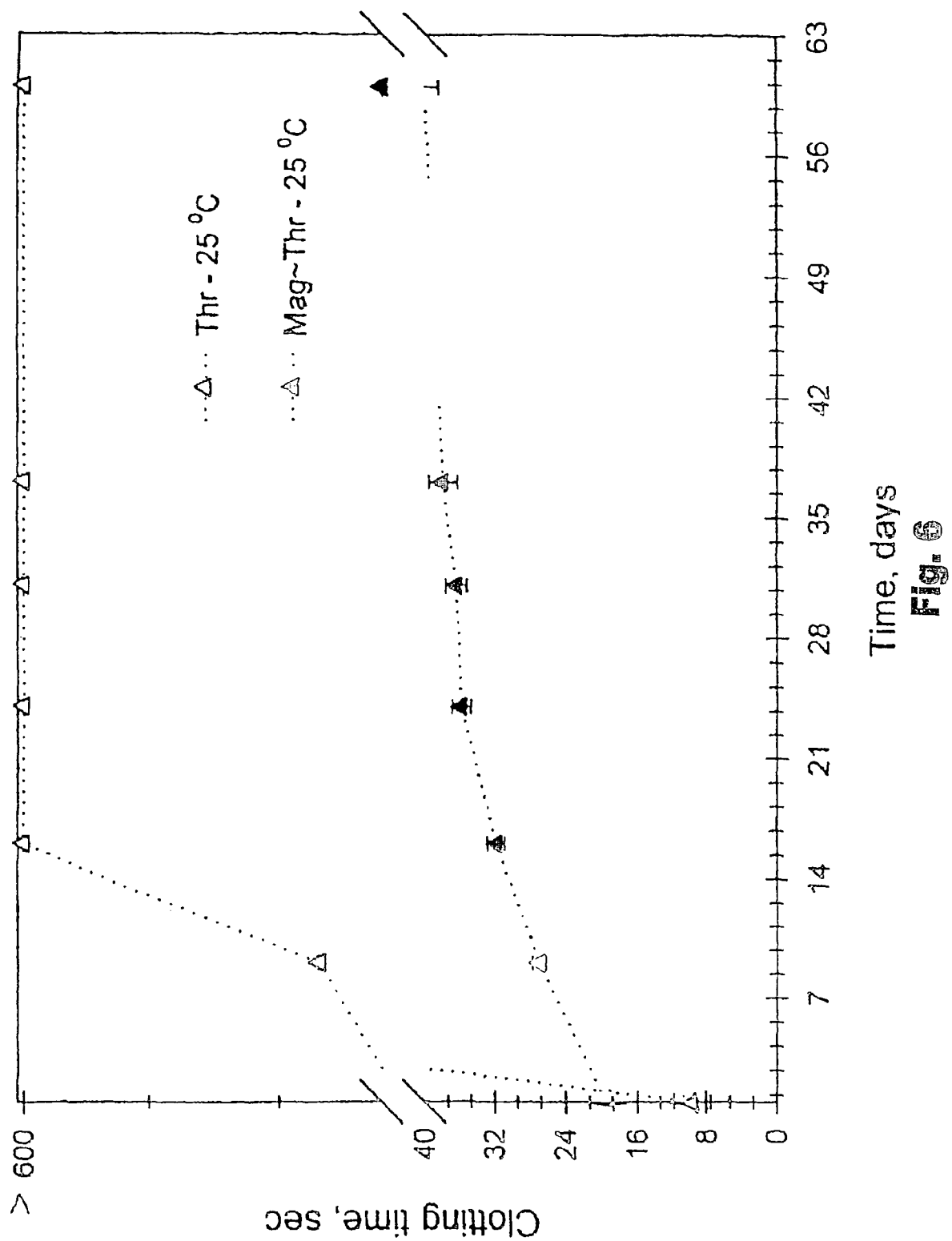
FIG. 6. Effect of sterilization on the clotting time in blood of Thr and Mag~Thr suspended in PBS and stored at RT.

FIG. 6 demonstrates the bacteria stability at 4° C. and RT obtained by immobilizing Thr to Mag nanoparticles (as shown by sterilizing the Thr and Mag~Thr suspension in PBS). For example, the clotting time in blood of sterilized Thr and Mag~Thr suspended in PBS and stored at RT for 37 days increased by more than 60 and 1.6, respectively.

Example 10

Effect of the ratio [Gelatin]/[Mag] on the Size and on the Clotting Time in Plasma and Blood of Lyophilized Mag~Thr Clotting time was measured at 37° C. by mixing 50 μl plasma (or blood) with samples containing, each sample, 10 μg of lyophilized immobilized Thr suspended in 100 μl 0.1M PBS (pH=7.4).

For lyophilization, samples containing 10 μg of immobilized Thr and different amounts of gelatin suspended in 100 μl 0.1M PBS were prepared. The samples were then dried by lyophilization. For clotting measurements, each dried sample was suspended with 100 µl H$_2$O. The results are shown in the following table.

TABLE 4

Effect of the ratio [Gelatin]/[Mag] on the size and on the clotting time in plasma and blood of lyophilized Mag~Thr.

| [Gelatin]/[Mag] (w/w) | Size (nm) | Clotting time in plasma (sec) | Clotting time in blood (sec) |
|---|---|---|---|
| 2 | 69 ± 11 | 26.6 ± 0.9 | 21.3 ± 1.9 |
| 1 | 68 ± 11 | 26.4 ± 0.2 | 18.5 ± 2.4 |
| 0.75 | 78 ± 14 | 26.6 ± 0.9 | 18.5 ± 2.2 |
| 0.5 | 89 ± 19 | 26.4 ± 0.7 | 18.5 ± 2.1 |
| 0.25 | 110 ± 21 | 27.1 ± 0.6 | 18.8 ± 1.8 |
| 0.05 | 124 ± 31 | 28.3 ± 0.6 | 19.4 ± 1.8 |
| 0.01 | 135 ± 34 | 34.6 ± 1.1 | 20.1 ± 1.9 |
| 0 | 154 ± 37 | 38.6 ± 1.4 | 24.1 ± 1.5 |

Table 4 illustrates a way to dry the Thr immobilized Mag nanoparticles while preserving the size and the hemostatic properties of these nanoparticles after resuspending them. Table 4 illustrates the following information:

1) Drying the Thr immobilized Mag nanoparticles by lyophilization leads to agglomeration, i.e. the average diameter of the Mag~Thr nanoparticles suspended in PBS increased from 70 nm to 154 nm due to lyophilization. Addition of gelatin to the Mag~Thr nanoparticles suspended in PBS, followed by lyophilization, decreased the size of the agglomerated Mag~Thr nanoparticles resuspended in PBS. For example, lyophilization of the Mag~Thr nanoparticles suspended in PBS in the presence of increasing gelatin concentration, i.e. at [Gelatin]/[Mag] ratio of 0.25, 0.75 and 1, leads, after resuspension in PBS of the dried nanoparticles, to an average size of 110, 78 and 68 nm, respectively.

2) The clotting time in plasma and blood of Mag~Thr nanoparticles suspended in PBS is preserved by adding to the nanoparticle suspension gelatin and then drying it by lyophilization.

Similar results to that described in Table 4 for the clotting time in plasma and blood were also obtained for SiO$_2$~Thr and AB~Thr.

Example 11

Effect of Lyophilization in the Absence or Presence of Gelatin on the Clotting Time in Plasma (A) and Blood (B) of Thr and Mag~Thr Suspended in PBS Clotting time was measured at 37° C. by mixing 50 µl plasma (or blood) with samples containing, each sample, 9.5 µg of lyophilized Thr or immobilized Thr suspended in 100 µl 0.1M PBS (pH=7.4).

For lyophilization, samples containing, each sample, 9.5 µg of Thr or immobilized Thr and 0.3 mg gelatin suspended in 100 µl 0.1M PBS were prepared. The samples were then dried by lyophilization. For clotting measurements, each dried sample was suspended with 100 µl H$_2$O. The results are shown in the following table.

TABLE 5

Effect of lyophilization in the absence or presence of gelatin on the clotting time in plasma (A) and blood (B) of Thr and Mag~Thr suspended in PBS

A

| Thrombin conjugated nanoparticle | Clotting time in plasma, sec | |
|---|---|---|
| | Before lyophilization | After lyophilization without gelatin |
| Mag~Thr | 31.4 ± 1.9 | 45.7 ± 2.1 |
| Thr | 11.5 ± 2.1 | >600 |

B

| Thrombin conjugated nanoparticle | Clotting time in blood, sec | |
|---|---|---|
| | Before lyophilization | After lyophilization with gelatin |
| Mag~Thr | 22.4 ± 2.1 | 22.4 ± 2.1 |
| Thr | 13.8 ± 2.2 | 24.8 ± 2.4 |

Table 5 demonstrates the effect of gelatin on the lyophilization stability of Thr and Mag~Thr nanoparticles suspended in PBS. Lyophilization caused a significant decrease in the clotting time of Thr suspension in PBS, i.e. in plasma, from 11.5 to >600 sec, and moderate decrease for Mag~Thr, i.e. from 31.4 to 45.7 sec. However, the addition of gelatin to the Thr solution in PBS moderated the decrease in the clotting time in plasma of the Thr (from 11.5 to 20.9 sec.), and preserved the clotting time of the Mag~Thr nanoparticles suspended in PBS.

A similar effect to that described in Table 5 was also obtained for SiO$_2$~Thr and AB~Thr.

Example 12

Effect of CaCl$_2$ on the Clotting Time in Plasma and Blood of Lyophilized Thr and Mag~Thr Clotting time was measured at 37° C. by mixing 50 µl plasma (or blood) with samples containing 5 µg of lyophilized Thr or immobilized Thr suspended in 100 µl 0.1M PBS (pH=7.4) in absence or presence of 8.3 mM CaCl$_2$.

For lyophilization, samples containing 5 µg of Thr or immobilized Thr and 0.27 mg of gelatin suspended in 100 µl 0.1M PBS were prepared. The samples were then dried by lyophilization. For clotting measurements, each dried sample was dispersed with 100 µl H$_2$O in the absence or presence of 8.3 mM CaCl$_2$. The results are shown in the following table.

TABLE 6

Effect of CaCl$_2$ on the clotting time in plasma and blood of lyophilized Thr and Mag~Thr.

| Thrombin conjugated nanoparticle | CaCl$_2$ (mM) | Clotting time in plasma (sec) | Clotting time in blood (sec) |
|---|---|---|---|
| Mag~Thr | 0 | 34.6 ± 0.9 | 23.3 ± 1.3 |
| Mag~Thr | 8.3 | 15.7 ± 0.4 | 12.6 ± 1.2 |
| Thr | 0 | 28.5 ± 0.5 | 30.6 ± 1.4 |
| Thr | 8.3 | 17.3 ± 0.2 | 20.9 ± 1.2 |

Table 6 illustrates the significant effect of $CaCl_2$, 8.3 mM, on the decrease in the clotting time in plasma and blood of Thr and Mag~Thr nanoparticles. For example, the measured clotting times in plasma and blood of resuspended lyophilized Mag~Thr suspension in PBS in absence and presence of 8.3 mM $CaCl_2$ were 34.6 and 23.3 sec., respectively in the absence of $CaCl_2$, and 15.7 and 12.6 sec., respectively in the presence of $CaCl_2$.

A similar effect to that described in Table 6 was also obtained for $SiO_2$~Thr and AB~Thr.

Example 13

Effect of Thrombin Concentration on the Clotting Time in Blood of Lyophilized Thr and Mag~Thr in the Presence of 8.3 mM of $CaCl_2$ Clotting time was measured at 37° C. by mixing 50 μl blood with samples containing, each sample, different amounts of lyophilized Thr or immobilized Thr in 100 μl 0.1M PBS (pH=7.4) in absence or presence of 8.3 mM $CaCl_2$.

For lyophilization, samples containing, each sample, different amounts of Thr or immobilized thrombin and appropriate amounts of gelatin suspended in 100 μl 0.1M PBS were prepared. The samples were then dried by lyophilization. For clotting measurements, each dried sample was dispersed with 100 μl $H_2O$ in absence or presence of 8.3 mM $CaCl_2$. The results are shown in FIG. 7.

Figure 7:
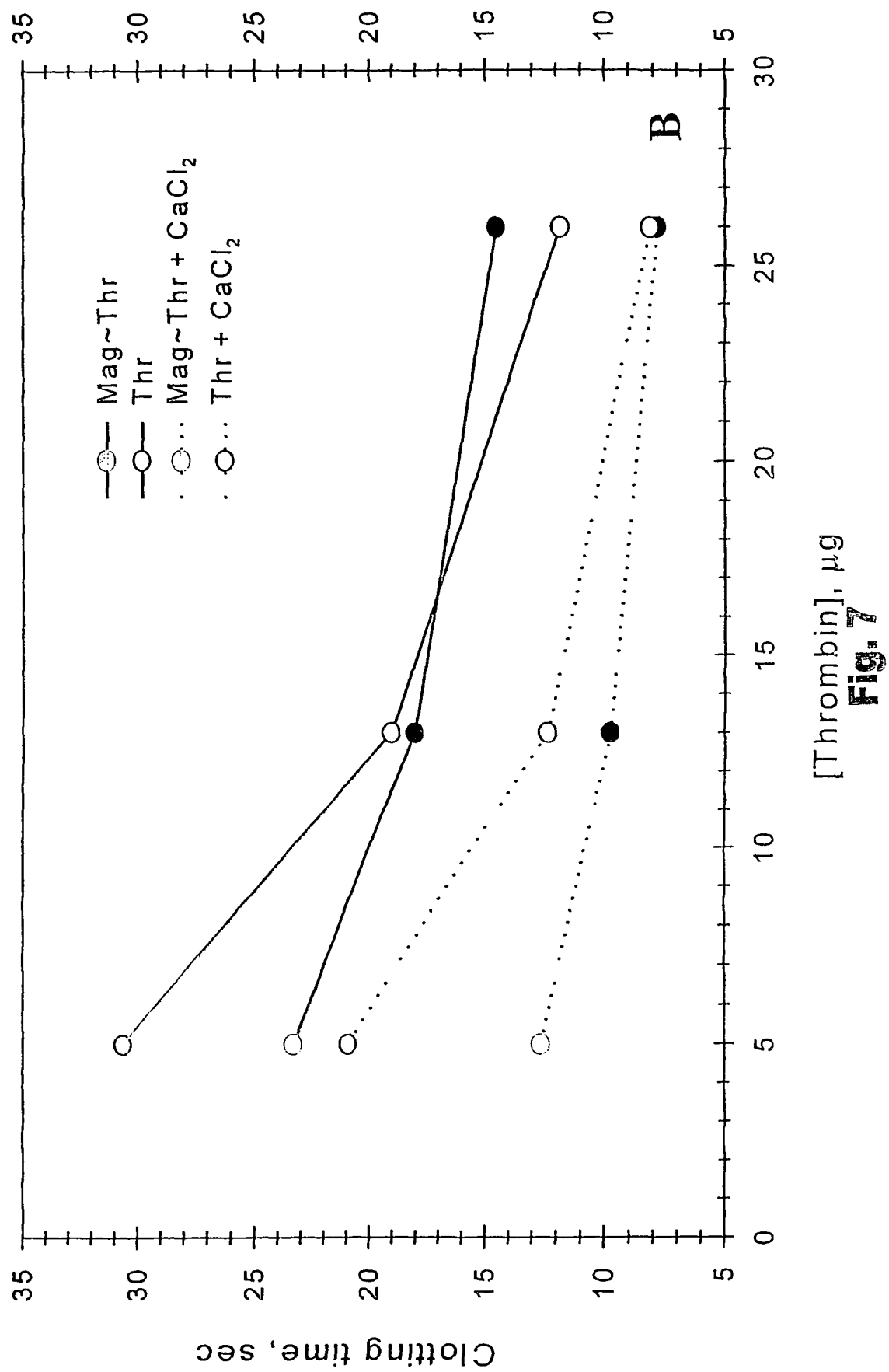
FIG. 7. Effect of $CaCl_2$ on the clotting time in blood of different concentrations of lyophilized Thr and Mag~Thr.

FIG. 7 also demonstrates the significant effect of 8.3 mM $CaCl_2$ on the decrease in the clotting time in blood of various concentrations of lyophilized Thr and Mag~Thr nanoparticles resuspended in PBS.

A similar effect to that described in FIG. 7 was also obtained for $SiO_2$~Thr and AB~Thr.

Example 14

Effect of Factor XIII on the Clotting Time in Plasma and Blood of Lyophilized Thr and Mag~Thr Clotting time was measured at 37° C. by mixing 50 μl plasma (or blood) with samples containing 13 μg of Thr or immobilized lyophilized Thr suspended in 100 μl 0.1M PBS (pH=7.4).

For lyophilization, samples containing 13 μg of Thr or immobilized thrombin and 0.35 mg of gelatin suspended in 100 μl 0.1M PBS were prepared. The samples were then dried by lyophilization. For clotting measurements, each dried sample was dispersed with 100 μl $H_2O$ in the presence of 8.3 mM $CaCl_2$. The results are shown in the following table.

TABLE 7

Effect of Factor XIII on the clotting time in plasma and blood of lyophilized Thr and Mag~Thr.

| Bioactive conjugate | [Factor XIII] (μg) | Clotting time in plasma (sec) | Clotting time in blood (sec) |
|---|---|---|---|
| Mag~Thr | 0 | 9.2 ± 0.8 | 8.7 ± 0.2 |
| Mag~Thr | 11.7 | 7.1 ± 0.7 | 6.4 ± 0.5 |
| Thr | 0 | 16.3 ± 0.4 | 23.8 ± 0.9 |
| Thr | 11.7 | 16.3 ± 0.3 | 18.2 ± 0.3 |

Table 7 demonstrates the effect of factor XIII on the decrease in the clotting time in plasma and blood of Thr and Mag~Thr nanoparticles. For example, the measured clotting times in plasma and blood of resuspended lyophilized Mag~Thr suspension in PBS containing 8.3 mM $CaCl_2$ in the absence and presence of factor XIII were 9.2 and 7.1 sec., respectively in plasma (23% decrease in clotting time), and 8.7 and 6.4 sec., respectively in blood (24% decrease in clotting time).

A similar effect to that described in Table 7 was also obtained for $SiO_2$~Thr and AB~Thr.

Example 15

In Vivo Trials

Rabbits (female, white, 2.5 Kg, New Zealand) were bled by pricking the main vein of the ear (with 18 G syringes) The bleeding rate was approximately 25 μl/sec. Attempts to stop the bleeding were made by placing (without pressure) a sterile cellulose bandage wetted with lyophilized Mag~Thr resuspened in PBS in the absence or presence of 8.3 mM $CaCl_2$ upon the wound. Similar trials were performed with cellulose dressings wetted with a Thr PBS solution in the absence or presence of 8.3 mM $CaCl_2$ (similar Thr concentration, 32 μg). Control trials were accomplished with cellulose dressings wetted only with PBS in absence or presence of 8.3 mM $CaCl_2$. A complete cessation of bleeding was observed after ca. 45 sec. for both dressings wetted with Thr or lyophilized Mag~Thr resuspended in PBS, and after ca. 30 sec. with dressings wetted with Thr or lyophilized Mag~Thr resuspended in PBS containing 8.3 mM $CaCl_2$. Conversely, the bleeding of the rabbit treated with the control dressing was not stopped by 2.5 min.; in order to prevent the rabbit from dying, the bleeding was ceased by applying strong pressure on the dressing located on the wound.

The above described experiment was performed, for each type of dressing, with 5 rabbits. Similar behavior was observed in each subject.

Similar trials were also performed with gelatin sponges (dressings). Similar behavior was also observed for each subject.

Similar trials to that described above substituting the Mag~Thr nanoparticles for AB~Thr were also performed. Similar behavior was also observed for each of the subjects tested.

Example 16

In Vivo Trials

Rabbits (female, white, 2.5 Kg, New Zealand) were bled by pricking the main vein of the ear (with 18 G syringes) The bleeding rate was approximately 25 μl/sec. Attempts to stop the bleeding were made by spraying, or dropping, upon the wound a PBS suspension of the lyophilized Mag~Thr nanoparticles in the absence or presence of 8.3 mM $CaCl_2$. Then, cellulose (or gelatin) dressings were placed (without pressure) upon the wound. Similar trials were performed with a Thr PBS solution in the absence or presence of 8.3 mM $CaCl_2$ (similar Thr concentration, 32 μg) Control trials were accomplished with PBS in the absence or presence of 8.3 mM $CaCl_2$. Similar behavior to that in described in example 15 was observed.

Similar trials to that described above substituting the Mag~Thr nanoparticles for AB~Thr were also performed. Similar behavior was also observed.

Example 17

Controlled Release

Fibrin glue containing antibiotics was prepared by shaking 10 mg of lyophilized Mag~Thr nanoparticles containing 1 mg antibiotics, i.e. Ampicillin sodium salt, with 0.5 ml of 0.1M PBS (pH=7.4) containing 0.2% fibrinogen for a few minutes at 37° C. The formed fibrin glue in 2 ml of 0.1M PBS (pH=7.4) was inserted into a dialysis membrane bag (cut off 10,000 m.w.), and then tightly sealed with a closure. The bag was immersed in 20 ml 0.1M PBS (pH=7.4) as release medium, and shaken at 37° C. in water bath. A 0.5 ml aliquot was withdrawn at each 0.5 h interval and an equal volume of fresh PBS was replaced. The concentration of Ampicillin sodium salt in the dialyzate (determined by UV spectrometry at 226 nm) increased gradually up to 7 h, and about 80% of Ampicillin sodium salt was released within 20 h.

A similar trial was also performed with AB~Thr nanoparticles containing Ampicillin sodium salt. A similar release profile was also observed.

Example 18

Targeting

Fibrin glue was prepared by shaking 10 mg of lyophilized Mag~Thr nanoparticles with 0.5 ml of 0.1M PBS (pH=7.4) containing 0.2% fibrinogen for a few minutes at 37 ° C. The formed fibrin glue was then placed in 2 ml of 0.1M PBS (pH=7.4). AB~Thr nanoparticles (1 mg) dispersed in 0.5 ml 0.1M PBS (pH=7.4) were then added to the formed fibrin glue in PBS. The mixture was then shaken at room temperature for 1 h. Excess AB~Thr nanoparticles were then removed from the fibrin glue by 4 centrifugation cycles in PBS. Light microscopy pictures visualized the binding of the AB-Thr nanoparticles to the surface of the biological glue. Similar behavior was also observed for the $SiO_2$~Thr nanoparticles (2.3 µm).

The invention claimed is:

1. Thrombin-conjugated nanoparticles, wherein said nanoparticles comprise one or more organic and/or inorganic compounds, wherein the nanoparticles are selected from the group consisting of magnetic iron oxide-containing nanoparticles, albumin nanoparticles, solid or hollow silica nanoparticles and nanoparticles made of organic polymeric core coated with a silica shell, optionally having magnetic layer interposed between said core and said silica shell.

2. The thrombin-conjugated nanoparticles according to claim 1, wherein the thrombin molecules are covalently-bonded to the surface of the nanoparticles.

3. The thrombin-conjugated nanoparticles according to claim 2, wherein the nanoparticles are magnetic iron oxide-containing nanoparticles having a coating on their surface, and wherein the thrombin molecules are covalently-liniked to said coating.

4. The thrombin-conjugated nanoparticles according to claim 1, wherein the thrombin molecules are covalently-bonded to spacer arms, and wherein said spacer arms are covalently-liniked to the surface of the nanoparticles.

5. The thrombin-conjugated nanoparticles according to claim 4, wherein the spacer arm is albumin.

6. The thrombin-conjugated nanoparticles according to claim 1, wherein the thrombin molecules are physically adsorbed onto spacer arms, and wherein said spacer arms are covalently-liniked to the surface of the nanoparticles.

7. The thrombin-conjugated nanoparticles according to claim 1, wherein the organic compounds are selected from the group consisting of proteins and synthetic polymers, and wherein the inorganic compounds are selected from the group consisting of metal oxides or oxides of metalloids.

8. The thrombin-conjugated nanoparticles according to claim 1, further comprising a pharmaceutical agent, wherein said pharmaceutical agent is either encapsulated within said nanoparticles, or bound thereto.

9. A therapeutic composition comprising a therapeutically effective amount of thrombin-conjugated nanoparticles as defined in claim 1, suitable for use in the preparation of fibrin-based biological sealant.

10. The therapeutic composition according to claim 9, provided in the form of a dry powder comprising thrombin-conjugated nanoparticles and a dispersant.

11. The therapeutic composition according to claim 10, wherein the dispersant is gelatin.

12. A therapeutic composition according to claim 9, provided in the form of a liquid vehicle comprising thrombin-conjugated nanoparticles and optionally a dispersant.

13. A therapeutic composition according to claim 9, which further comprises one or more additives selected from the group consisting of Ca salts, factor XIII and antifibrinolytic agents.

14. The thrombin-conjugated nanoparticles according to claim 1, wherein the thrombin molecules are:
   (a) covalently-bonded to the surface of the nanoparticles; or
   (b) covalently-bonded to spacer arms, wherein said spacer arms are covalently-liniked to the surface of the nanoparticles; or
   (c) physically adsorbed onto a spacer arm, wherein said spacer arm is albumin, further wherein said albumin is covalently-liniked to the surface of the nanoparticles.

* * * * *